(12) United States Patent
Loebermann et al.

(10) Patent No.: US 6,686,474 B2
(45) Date of Patent: Feb. 3, 2004

(54) PROCESS FOR THE PRODUCTION OF ANTIULCERATIVES

(75) Inventors: Hartmut Loebermann, Aachen (DE); Karl-Heinz Caster, Eschweiler (DE)

(73) Assignee: Gruenenthal GmbH, Aachen (DE)

( * ) Notice: Subject to any disclaimer, the term of this patent is extended or adjusted under 35 U.S.C. 154(b) by 78 days.

(21) Appl. No.: 10/133,644

(22) Filed: Apr. 29, 2002

(65) Prior Publication Data

US 2002/0183363 A1 Dec. 5, 2002

Related U.S. Application Data

(63) Continuation of application No. PCT/EP00/10580, filed on Oct. 27, 2000.

(30) Foreign Application Priority Data

Oct. 28, 1999 (DE) .......................... 199 51 960

(51) Int. Cl.[7] .............................................. C07D 401/12
(52) U.S. Cl. ................................................... 546/273.7
(58) Field of Search ...................................... 546/273.7

(56) References Cited

U.S. PATENT DOCUMENTS 4,619,997 A    10/1986   Sih

FOREIGN PATENT DOCUMENTS

| EP | 0005129 | 4/1981 |
|---|---|---|
| EP | 0240158 | 4/1991 |
| EP | 0484265 | 5/1992 |
| EP | 0302720 | 11/1992 |
| EP | 0533264 | 11/1999 |
| EP | 0 533 264 | * 11/1999 |
| GB | 2239453 | 7/1991 |
| WO | WO 91/18895 | 12/1991 |
| WO | WO 97/22603 | 6/1997 |
| WO | WO 98/09962 | 3/1998 |

* cited by examiner

*Primary Examiner*—D. Margaret Seaman
(74) *Attorney, Agent, or Firm*—Crowell & Moring LLP

(57) ABSTRACT

A method for the production of an antiulcerative via reacting reacting a compound of formula II:

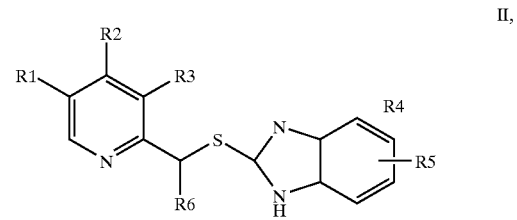

with m-chloroperoxybenzoic acid in a solvent of acetone or acetone/water mixture to form a reaction mixture. The reaction mixture has a pH of 7.0 or above, and crystals of the antiulcerative compound of formula I are formed which may be optionally separated.

41 Claims, No Drawings

PROCESS FOR THE PRODUCTION OF ANTIULCERATIVES

CROSS REFERENCE TO RELATED APPLICATIONS

The present application is a continuation of international patent application no. PCT/EP00/10580, filed Oct. 27, 2000, designating the United States of America, the entire disclosure of which is incorporated herein by reference. Priority is claimed based on Federal Republic of Germany patent application no. 199 51 960.9, filed Oct. 28, 1999.

BACKGROUND OF THE INVENTION

This invention relates to a process for the production of benzimidazole derivatives suitable as antiulceratives, in particular omeprazole or pantoprazole.

Antiulceratives are today used on a large scale for the treatment of ulcers, in particular stomach ulcers (gastric ulcers). There are many different causes for stomach ulcers and many people are prescribed drugs to provide relief. Treatment is usually with substances which inhibit the proton pumps, $H^+K^+ATPase$, located in the stomach wall. Known representatives of this therapeutic category are 5-methoxy-2-[(4-methoxy-3,5-dimethyl-2-pyridinyl) methyl]sulfinyl-1H-benzimidazole, generic name omeprazole, and 5-(difluoromethoxy)-2-[3,4-dimethoxy-2-pyridyl)methylsulfinyl]benzimidazole, generic name pantoprazole. Omeprazole in particular is a known proton pump inhibitor, for which a considerable number of production processes have been developed. The synthesis of omeprazoles and structurally related compounds typically comprises several stages. In the case of omeprazole of 5-methoxy-2-[(4-methoxy-3,5-dimethyl-2-pyridinyl) methylthio]-1H-benzimidazole, which is also known as pyrmetazole, the final step is usually oxidation of a sulfide, to yield the corresponding sulfinyl, in particular to yield omeprazole. This final oxidation step is of great significance to the yield, purity and also economic viability of the entire production process and various proposals have accordingly been made in the prior art for this synthesis step.

In EP 0 005 129, which claimed protection for the substance omeprazole, oxidation is described as with the assistance of oxidising agents such as m-chloroperbenzoic acid in a solvent. This solvent is not specified in any further detail, but the Examples only make reference to trichloromethane, ethanol, benzene and hydrochloric acid. Yields and product purity were, however, not satisfactory.

EP 0 533 264 discloses an oxidation process in which magnesium ammonoperoxyphthalate is used. This reaction conventionally performed in solvents which contain water, water-miscible solvents or water-immiscible solvents, or preferably, combinations of these three types of solvent. Various solvents are listed, for example low molecular weight alcohols as the water-miscible solvent and toluene as the water-immiscible solvent. However, neither ketones nor explicitly acetone are mentioned and also not preferred.

EP 0 484 265 describes various possibilities for the production of omeprazole, wherein the last reaction step, the oxidation of pyrmetazole to omeprazole is performed with a per-acid, preferably m-chloroperbenzoic acid, in an acidic medium with pyrmetazole salts, if the solvent is not methanol. In contrast, when methanol is used, as is preferred, pyrmetazole is used and the oxidation is performed with hydrogen peroxide in the presence of a catalyst such as ammonium molybdate and an inorganic base.

EP 302 720 describes oxidation with hydrogen peroxide in the presence of vanadium compounds. This document lists a series of compounds as solvents, among which ethanol, methanol, acetone and acetonitrile are preferred. Although acetone is used in this case, the use of hydrogen peroxide with a catalyst is disclosed as essential to the invention. This constitutes the nub of the inventive concept of said application.

GB 2 239 453 furthermore describes the oxidation of pyrmetazole by photochemical oxidation by exciting appropriate compounds with light in order to oxidise pyrmetazole to yield omeprazole.

WO 98/09962 describes an oxidation with peroxyacetic acid in a two-phase medium of water and a chlorinated organic solvent at an alkaline pH. Dichloromethane is stated to be particularly preferred in this case.

WO 91/18895 corresponds to European patent EP 0 533 752. This document describes oxidation with m-chloroperoxybenzoic acid in an inert solvent, wherein methylene chloride is preferred, at a pH of around 8.0 to 8.6, wherein the actual essence of the reaction is the addition of alkyl formate to the aqueous phase. In this case too, acetone is not mentioned at all and, in principle, the route via chloroperoxybenzoic acid in dichloromethane already known from EP 0533752 is adopted.

WO 97/22603 discloses a process in which the final reaction steps are all performed in the same solvent system. Oxidation is here again performed with m-chloroperoxybenzoic acid. Preferred solvent systems are media immiscible with water, for example carbon tetrachloride, trichloroethane, chloroform, methylene chloride or toluene. Toluene is in particular preferred in this process.

EP 240 158 relates to benzimidazole derivatives as antiulceratives. In this case, oxidation is performed with per-compounds, such as m-chloroperoxybenzoic acid, in halogenated hydrocarbons, such as chloroform or dichloromethane, and/or alcohols, such as methanol, ethanol or butanol.

U.S. Pat. No. 4,619,997 discloses corresponding benzimidazole derivatives, in which the derivatives are oxidised with any known oxidising agents, in particular peroxy acids, but also for example with hypochlorite solution. The reaction preferably proceeds in inert solvents, such as benzene, methylene chloride or chloroform.

Further relevant documents in this connection are ES 539 739, in which iodosobenzene and iodosotoluene are proposed as oxidising agents, and ES 543 816, which proposed m-chloroperoxybenzoic acid in powder form for the oxidation.

The large number of proposed process variants alone makes it clear that there is further need for improvement. The majority of these processes known from the prior art thus exhibit the disadvantage that they often give rise to low yields, in particular of omeprazole, or that the omeprazole obtained is contaminated with starting materials or secondary products. A common feature, however, is that, even if these disadvantages are not so pronounced, all the preferred or explicitly described production processes are performed with chlorinated organic solvents such as dichloromethane or trichloromethane or other compounds such as toluene which are undesirable from an environmental or medical standpoint. All these compounds are known to have a negative impact on the environment and as more stringent regulatory requirements are being imposed and the costs that are inevitably associated therewith, there is thus a clear need to bring about an improvement in comparison with the prior art.

SUMMARY AND DETAILED DESCRIPTION OF THE INVENTION

The object of the present invention is accordingly to provide a process for the production of benzimidazole derivatives, in particular omeprazole and pantoprazole, suitable as antiulceratives, which process, while achieving elevated yields and high purity of the final products, allows solvents to be used which are more compatible with environmental and health concerns.

The present application accordingly provides a first process for the production of antiulceratives of the formula I:

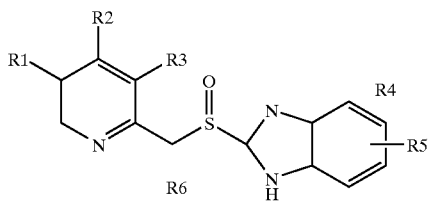

in which
$R^1$, $R^2$ and $R^3$ are independently selected from
  hydrogen,
  C1–C8 alkyl,
  C3–C8 cycloalkyl,
  C2–C8 fluoroalkyl and
  C1–C8 alkoxy,
$R^4$ and $R^5$ are independently selected from
  hydrogen,
  C1–C8 alkyl,
  C3–C8 cycloalkyl,
  CH$_2$–C3–C8 cycloalkyl,
  C1–C8 alkoxycarbonyl,
  C1–C8 alkoxy,
  C1–C8 fluoroalkoxy,
  CF$_3$,
  C2–C8 fluoroalkyl and
  —C(O)O—C1–C8 alkyl, and
$R^6$ is selected from
  hydrogen and
  C1–C2 alkyl,
in which process a compound of the formula II:

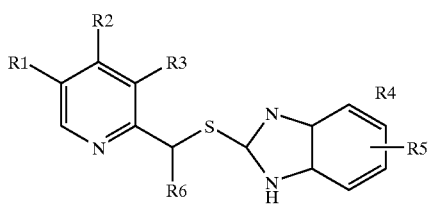

in which $R^1$, $R^2$, $R^3$, $R^4$, $R^5$ and $R^6$ have the above-stated meaning, is reacted with oxidising agents, in particular peroxy compounds, preferably m-chloroperoxybenzoic acid, in a solvent. A catalyst may optionally be added during said reaction. The pH of this reaction mixture is then raised to above pH 7.0, the solvent is optionally removed and then the crystals of the compound of the formula I are separated, wherein the stated solvent is acetone or an acetone/water mixture.

The present application also provides a second process for the production of antiulceratives of the formula I:

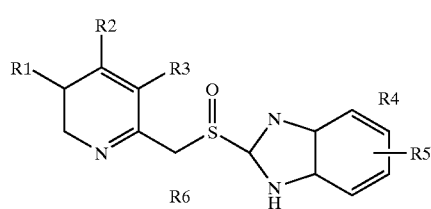

in which
$R^1$, $R^2$ and $R^3$ are independently selected from
  hydrogen,
  C1–C8 alkyl,
  C3–C8 cycloalkyl,
  C2–C8 fluoroalkyl and
  C1–C8 alkoxy,
$R^4$ and $R^5$ are independently selected from
  hydrogen,
  halogen
  C1–C8 alkyl,
  C3–C8 cycloalkyl,
  CH$_2$–C3–C8 cycloalkyl,
  C1–C8 alkoxycarbonyl,
  C1–C8 alkoxy,
  C1–C8 fluoroalkoxy,
  CF$_3$,
  C2–C8 fluoroalkyl and
  —C(O)O—C1–C8 alkyl, and
$R^6$ is selected from
  hydrogen and
  C1–C2 alkyl,
in which process a compound of the formula II:

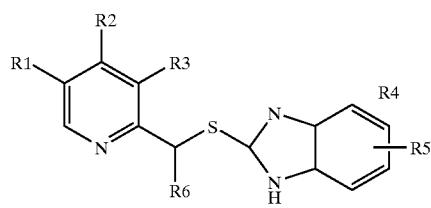

in which $R^1$, $R^2$, $R^3$, $R^4$, $R^5$ and $R^6$ have the above-stated meaning is reacted with oxidising agents, in particular peroxy compounds, preferably m-chloroperoxybenzoic acid, in a solvent with a pH of >7.0. A catalyst may optionally be added during said reaction. Water is then optionally added, the solvent is optionally removed and then the crystals of the compound of the formula I are separated, wherein the stated solvent is acetone or an acetone/water mixture.

The advantage of both processes in comparison with the prior art resides in the use of acetone or acetone/water mixtures as the solvent for the oxidation reaction. In comparison with the solvents hitherto described in the prior art, in particular for omeprazole, acetone is a solvent which is known not to be hazardous to the environment and also has a distinct health advantage with its maximum allowable concentration (MAC) value of 1000 ppm (in comparison with toluene's MAC value of 100 ppm). The proposed processes using acetone or acetone/water mixtures as the solvent simultaneously permit the production of the products of the process at elevated purity and yield. The inventive process is accordingly also advantageous in this respect.

Any oxidising agent known to the person ordinarily skilled in the art may be used as the oxidising agent, in particular peroxy compounds such as peroxides, per-acids or per-esters, with hydrogen peroxide and in particular m-chloroperoxybenzoic acid being preferred among these. The term peroxy compounds is taken to mean compounds which comprise at least one peroxy group.

The catalysts optionally added in the processes according to the invention may be catalysts for oxidation reactions known to the person skilled in the art, in particular inorganic acids and others. In particularly preferred embodiments of the processes of the present invention, however, no catalysts are added to the reaction mixture, especially when m-chloroperoxybenzoic acid or hydrogen peroxide is used. For the purposes of this invention, the term reaction mixture should be taken to mean the mixture of a compound according to the formula II and the oxidising agent, in particular the peroxy compound, preferably m-chloroperoxybenzoic acid, in acetone or an acetone/water mixture, optionally of a pH of >7.0.

With regard to the second process described above, it is particularly preferred to maintain the pH of the solvent and thus of the reaction mixture at a value of >7.0 by pH-static titration, preferably with NaOH, and/or by buffer substances, preferably mono- or dibasic salts, in particular sodium or potassium carbonate and/or sodium or potassium bicarbonate, dissolved in or added to the solvent. It is also preferred in the case of anhydrous acetone to add buffer substances which, in the case of the optional, but preferred, addition of water in the second process may immediately act as buffer substances and thus prevent an acidic pH from occurring in the resultant solvent mixture. Many of the antiulceratives which may be produced using the process according to the invention, in particular the preferred omeprazole and pantoprazole, are highly acid-sensitive.

The present invention particularly preferably provides processes according to the invention as described above in which in the compounds according to the formulae I and II, $R^1$ means $CH_3$, $R^2$ means $OCH_3$, $R^3$ means $CH_3$, $R^4$ means H, $R^5$ means $OCH_3$ in position 5 and $R^6$ means H.

The corresponding compound according to the formula I is omeprazole, that according to the formula II is pyrmetazole.

The present invention furthermore provides processes according to the invention as described above, in which in the compounds according to the formulae I and II, $R^1$ means H, $R^2$ means $OCH_3$, $R^3$ means $OCH_3$, $R^4$ means H, $R^5$ means $OCF_2H$ in position 5 and $R^6$ means H.

The corresponding resultant compound according to the formula I is pantoprazole.

When an acetone/water mixture is used as the solvent in the reaction mixture, water is conventionally used in a ratio by volume of 1% to 50% (v/v), preferably of 5% to 20% (v/v), in particular of 10% to 15% (v/v).

It is furthermore preferred to adjust the reaction mixture to a temperature of between −20° C. and 30° C., preferably of between −5° C. and 5° C., in particular during the oxidation reaction, optionally, in particular to protect the products, but also throughout the process described herein.

In the processes according to the invention, the molar ratio between the compound of the formula II and the peroxy compound, preferably m-chloroperoxybenzoic acid, is conventionally 1:0.7 to 1.4, preferably 1:0.9 to 1.2, in particular 1:1.

Removal of the solvent, which is optional in both processes, is performed using processes familiar to the person ordinarily skilled in the art, wherein it is in particular preferred to remove the solvent (drying) under reduced pressure, for example by applying a vacuum, in particular at temperatures of below room temperature, preferably of around 0° C. This method is particularly mild for antiulceratives, in particular for omeprazole or pantoprazole.

In the processes according to the invention, the solvent is preferably removed when it comprises an acetone/water mixture. When pure acetone is used, in particular in accordance with the first described process, it is possible to obtain crystals of the corresponding antiulcerative, for example of omeprazole, without removing the solvent and thus to separate the crystals directly. In a corresponding further preferred embodiment of the first process, removal of the solvent is accordingly omitted.

In the method according to the first process, the reaction step stated therein in which the pH of the reaction mixture is increased to above 7.0 is performed using methods known to the person ordinarily skilled in the art. It is, however, in particular preferred to add basic substances and/or solutions of these substances, in particular solutions of NaOH, sodium or potassium carbonate or sodium or potassium bicarbonate, which preferably have a concentration of >1.0 M.

The following Examples illustrate the invention, without limiting it thereto.

EXAMPLES

Example 1

0.05 mol of pyrmetazole was dissolved in acetone and 0.05 mol of m-chloroperoxybenzoic acid (8.6 g) was then added to this solution. The temperature of the reaction mixture was maintained at around 0° C. during addition until the end of the reaction. On completion of the addition of the m-chloroperoxybenzoic acid, a white crystalline precipitate had formed. A 1.0 M potassium carbonate solution in water was then added in order to increase the pH to above 7.0. The crystals were then separated and washed with acetone and water. The washed crystals were dried under a vacuum.
Yield: 78.7% (13.6 g)

Example 2

0.05 mol of pyrmetazole was dissolved in an acetone/water mixture with a water content of 10% (v/v) and 0.05 mol of m-chloroperoxybenzoic acid (8.6 g) were then added to this solution. The temperature of the reaction mixture was maintained at approx. −3° C. during addition until the end of the reaction. On completion of the addition of the m-chloroperoxybenzoic acid, a 5.0 M NaOH solution was added in order to increase the pH to above 7.0. The solvent was then removed under reduced pressure, resulting in the formation of a white crystalline precipitate. The crystals were separated and washed with acetone and water. The washed crystals were dried under a vacuum.
Yield: 76% (13.1 g)

Example 3

0.05 mol of pyrmetazole was dissolved in an acetone/water mixture containing 15% (v/v) of water. The solvent had a pH of above 7.0, which was maintained by the presence of 0.055 mol of sodium bicarbonate (5.5 g). 0.05 mol of m-chloroperoxybenzoic acid (8.6 g) was then added and the mixture reacted. The temperature of the reaction mixture was maintained at around 0° C. during the addition and until the end of the reaction. After addition of m-chloroperoxybenzoic acid, additional water was added and the solvent was then removed under reduced pressure, resulting in the formation of a white crystalline precipitate. The crystals were separated and washed with acetone and water. The washed crystals were dried under a vacuum. Yield: 81% (14.0 g)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. A method for the production of an antiulcerative of formula I:

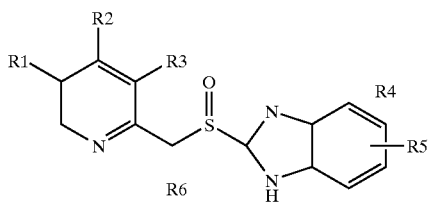

wherein $R^1$, $R^2$ and $R^3$ are independently selected from the group consisting of hydrogen, C1–C8 alkyl, C3–C8 cycloalkyl, C2–C8 fluoroalkyl and C1–C8 alkoxy, $R^4$ and $R^5$ are independently selected from the group consisting of hydrogen, C1–C8 alkyl, C3–C8 cycloalkyl, $CH_2$—C3–C8 cycloalkyl, C1–C8 alkoxycarbonyl, C1–C8 alkoxy, C1–C8 fluoroalkoxy, $CF_3$, C2–C8 fluoroalkyl and C(O)O—C1–C8 alkyl, and $R^6$ is hydrogen or C1–C2 alkyl, wherein the method comprises reacting a compound of formula II:

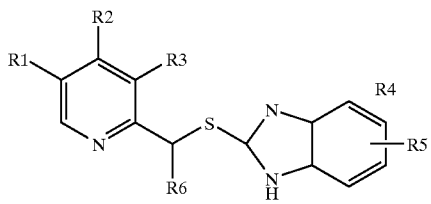

wherein $R^1$, $R^2$, $R^3$, $R^4$, $R^5$ and $R^6$ are defined as above, with m-chloroperoxybenzoic acid in a solvent selected from the group consisting of acetone and acetone/water mixture to form a reaction mixture, raising the pH of the reaction mixture to above pH 7.0, whereby crystals of the compound of formula I are formed, and separating the crystals of the compound of formula I.

2. A method according to claim 1, wherein the solvent is removed prior to separating the crystals of the compound of formula I.

3. A method according to claim 1, wherein the pH of the solvent is maintained at a value of $\geq 7.0$ by pH-static titration, or by addition of a buffer substance or a buffer solution, or by both.

4. A method according to claim 3, wherein the pH-static titration is with NaOH.

5. A method according to claim 4, wherein the NaOH is in solution.

6. A method according to claim 5, wherein the NaOH solution has a concentration of at least 1.0 M.

7. A method according to claim 3, wherein the buffer substance is selected from the group consisting of monobasic salts and dibasic salts.

8. A method according to claim 7, wherein the monobasic salt is sodium or potassium carbonate, and the dibasic salt is sodium or potassium bicarbonate.

9. A method according to claim 3, wherein the buffer solution is a solution of sodium carbonate, potassium carbonate, sodium bicarbonate or potassium bicarbonate with a concentration of at least 1.0 M.

10. A method according to claim 1, wherein in formula I and II, $R^1$ is $CH_3$, $R^2$ is $OCH_3$, $R^3$ is $CH_3$, $R^4$ is H, $R^5$ is $OCH_3$ in position 5 and $R^6$ is H; or $R^1$ is H, $R^2$ is $OCH_3$, $R^3$ is $OCH_3$, $R^4$ is H, $R^5$ is $OCF_2H$ in position 5 and $R^6$ is H.

11. A method according to claim 1, wherein the solvent is an acetone/water mixture containing 1%–50% (v/v) water.

12. A method according to claim 11, wherein the acetone/water mixture contains 5%–20% (v/v) water.

13. A method according to claim 12, wherein the acetone/water mixture contains 10%–15% (v/v) of water.

14. A method according to claim 1, wherein the temperature of the reaction mixture is maintained between –20° C. and 30° C. when a compound of the formula II is reacted with m-chloroperoxybenzoic acid.

15. A method according to claim 14, wherein the temperature of the reaction mixture is maintained between –20° C. and 30° C. throughout the entire method.

16. A method according to claim 14, wherein the temperature of the reaction mixture is maintained between –5° C. and 5° C.

17. A method according to claim 16, wherein the temperature of the reaction mixture is maintained between –5° C. and 5° C. throughout the entire method.

18. A method according to claim 1, wherein the molar ratio between the compound of the formula II and m-chloroperoxybenzoic acid is from 1:0.7 to 1:1.4.

19. A method according to claim 18, wherein the molar ratio between the compound of the formula II and m-chloroperoxybenzoic acid is from 1:0.9 to 1:1.2.

20. A method according to claim 2, wherein the solvent is removed under reduced pressure.

21. A method for the production of an antiulcerative of formula I:

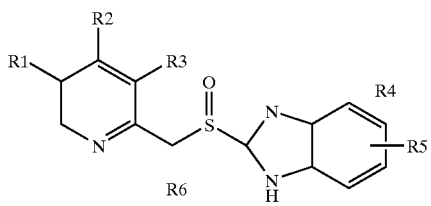

wherein
R$^1$, R$^2$ and R$^3$ are independently selected from the group consisting of hydrogen, C1–C8 alkyl, C3–C8 cycloalkyl, C2–C8 fluoroalkyl and C1–C8 alkoxy,
R$^4$ and R$^5$ are independently selected from the group consisting of hydrogen, halogen, C1–C8 alkyl, C3–C8 cycloalkyl, CH$_2$—C3–C8 cycloalkyl, C1–C8 alkoxycarbonyl, C1–C8 alkoxy, C1–C8 fluoroalkoxy, CF$_3$, C2–C8 fluoroalkyl and C(O)O—C1–C8 alkyl, and
R$^6$ is hydrogen or C1–C2 alkyl,
wherein the method comprises
reacting a compound of formula II:

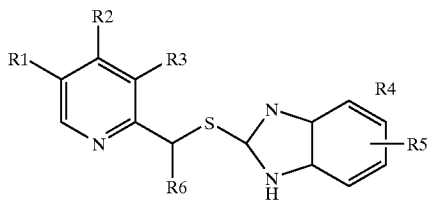

wherein R$^1$, R$^2$, R$^3$, R$^4$, R$^5$ and R$^6$ are defined as above,
with m-chloroperoxybenzoic acid in a solvent selected from the group consisting of acetone and acetone/water mixture with a pH of ≧7.0 to form crystals of the compound of formula I, and
separating the crystals.

22. A method according to claim 21, wherein water is added after the compound of formula II is reacted with m-chloroperoxybenzoic acid in a solvent.

23. A method according to claim 21, wherein the solvent is removed prior to separating the crystals of the compound of the formula I.

24. A method according to claim 21, wherein the pH of the solvent is maintained at a value of ≧7.0 by pH-static titration, or by addition of a buffer substance or a buffer solution, or by both.

25. A method according to claim 24, wherein the pH-static titration is with NaOH.

26. A method according to claim 25, wherein the NaOH is in solution.

27. A method according to claim 26, wherein the NaOH solution has a concentration of at least 1.0 M.

28. A method according to claim 25, wherein the buffer substance is selected from the group consisting of monobasic salts and dibasic salts.

29. A method according to claim 28, wherein the monobasic salt is sodium or potassium carbonate, and the dibasic salt is sodium or potassium bicarbonate.

30. A method according to claim 24, wherein the buffer solution is a solution of sodium carbonate, potassium carbonate, sodium bicarbonate or potassium bicarbonate with a concentration of at least 1.0 M.

31. A method according to claim 21, wherein in formulas I and II,
R$^1$ is CH$_3$, R$^2$ is OCH$_3$, R$^3$ is CH$_3$, R$^4$ is H, R$^5$ is OCH$_3$ in position 5 and R$^6$ is H; or
R$^1$ is H, R$^2$ is OCH$_3$, R$^3$ is OCH$_3$, R$^4$ is H, R$^5$ is OCF$_2$H in position 5 and R$^6$ is H.

32. A method according to claim 21, wherein the solvent is an acetone/water mixture containing 1%–50% (v/v) water.

33. A method according to claim 32, wherein the acetone/water mixture contains 5%–20% (v/v) water.

34. A method according to claim 33, wherein the acetone/water mixture contains 10%–15% (v/v) of water.

35. A method according to claim 21, wherein the temperature of the reaction mixture is maintained between −20° C. and 30° C. when a compound of the formula II is reacted with m-chloroperoxybenzoic acid.

36. A method according to claim 35, wherein the temperature of the reaction mixture is maintained between −20° C. and 30° C. throughout the entire method.

37. A method according to claim 35, wherein the temperature of the reaction mixture is maintained between −5° C. and 5° C.

38. A method according to claim 37, wherein the temperature of the reaction mixture is maintained between −5° C. and 5° C. throughout the entire method.

39. A method according to claim 21, wherein the molar ratio between the compound of the formula II and m-chloroperoxybenzoic acid is from 1:0.7 to 1:1.4.

40. A method according to claim 39, wherein the molar ratio between the compound of the formula II and m-chloroperoxybenzoic acid is from 1:0.9 to 1:1.2.

41. A method according to claim 23, wherein the solvent is removed under reduced pressure.

* * * * *